(12) United States Patent
Sudo et al.

(10) Patent No.: US 8,066,663 B2
(45) Date of Patent: Nov. 29, 2011

(54) SLIDE VALVES EQUIPPED IN A SYRINGE AND THUS EQUIPPED SYRINGE

(75) Inventors: Masamichi Sudo, Tokyo (JP); Nobuo Sudo, Tokyo (JP)

(73) Assignee: Daikyo Seiko Ltd., Tokyo (JP)

( * ) Notice: Subject to any disclaimer, the term of this patent is extended or adjusted under 35 U.S.C. 154(b) by 0 days.

(21) Appl. No.: 12/452,177

(22) PCT Filed: Jun. 20, 2008

(86) PCT No.: PCT/JP2008/061685
§ 371 (c)(1),
(2), (4) Date: Dec. 18, 2009

(87) PCT Pub. No.: WO2008/156216
PCT Pub. Date: Dec. 24, 2008

(65) Prior Publication Data
US 2010/0106086 A1    Apr. 29, 2010

(30) Foreign Application Priority Data
Jun. 20, 2007    (JP) ................................ 2007-163116

(51) Int. Cl.
*A61M 37/00*    (2006.01)
(52) U.S. Cl. ......................................................... 604/89
(58) Field of Classification Search .................. 604/83, 604/89, 207, 249
See application file for complete search history.

(56) References Cited

U.S. PATENT DOCUMENTS

| 5,665,068 A | * | 9/1997 | Takamura | 604/90 |
| 5,899,881 A | * | 5/1999 | Grimard et al. | 604/89 |
| 2006/0173409 A1 | | 8/2006 | Yang | |

FOREIGN PATENT DOCUMENTS

| JP | S62-139668 | 6/1987 |
| JP | U-H02-58446 | 4/1990 |
| JP | H09-206377 | 9/1997 |
| JP | 2000-110888 | 4/2000 |
| JP | 2005-160888 | 6/2005 |

* cited by examiner

*Primary Examiner* — Nicholas Lucchesi
*Assistant Examiner* — Weng Lee
(74) *Attorney, Agent, or Firm* — Manabu Kanesaka

(57) ABSTRACT

There are provided an intermediate slide valve as well as a plunger slide valve equipped in a syringe in direct contact with injection liquids and a syringe equipped with such slide valves, the injection liquids nor valves being not affected with each other.

The intermediate slide valve 10 equipped in the syringe 10 comprises an approximately cylindrical first elastic body 13 and an approximately cylindrical second elastic body 14 which is jointed with one bottom surface 13c of the first elastic body 13, the other bottom surface 13a of the first elastic body 13 and a side surface portion continued therefrom being laminated with a synthetic resin film 15 and the other bottom surface 14a of the second elastic body 14 and a side surface portion continued therefrom be laminated with a synthetic resin film 16.

10 Claims, 4 Drawing Sheets

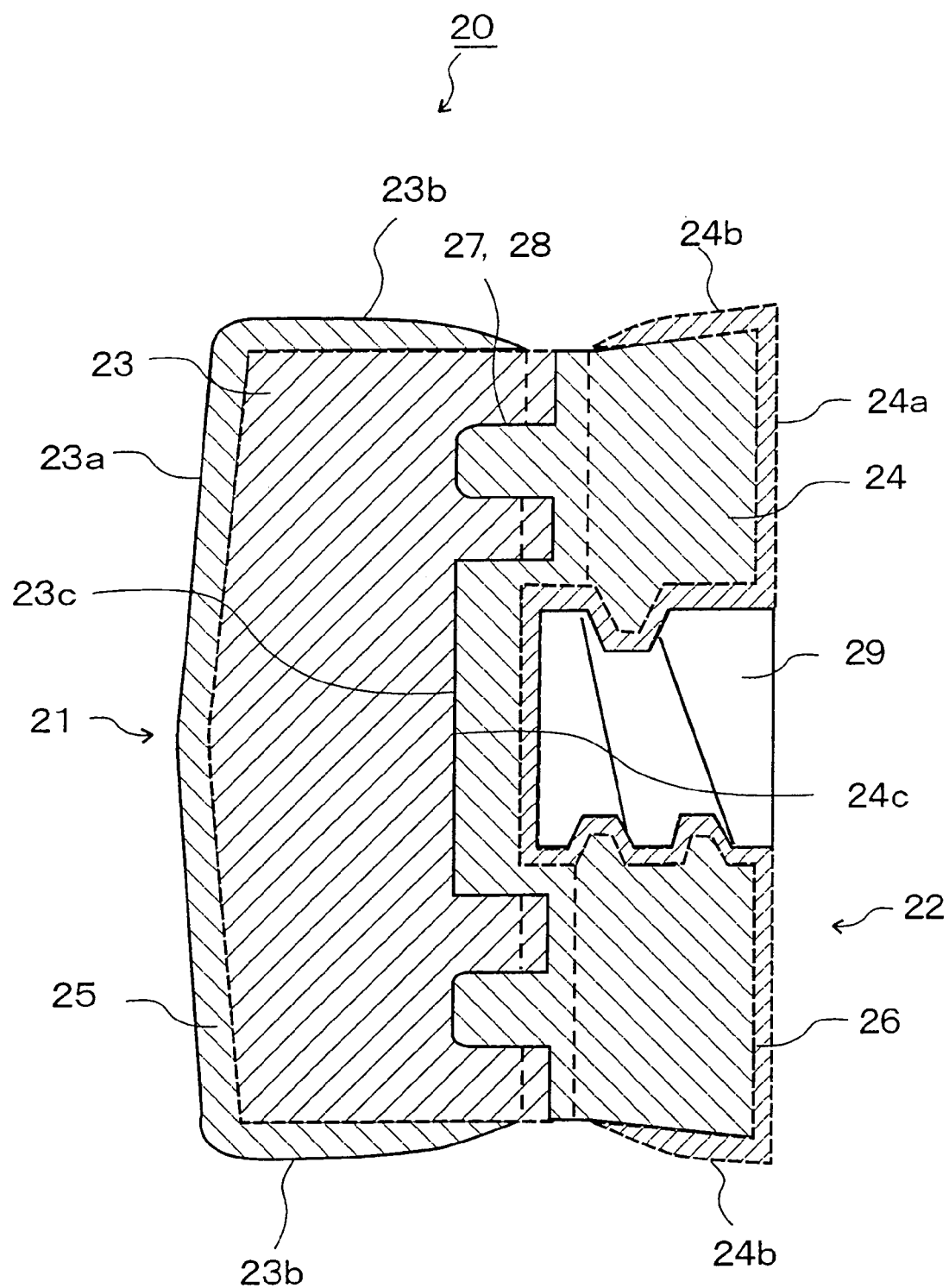

SLIDE VALVES EQUIPPED IN A SYRINGE AND THUS EQUIPPED SYRINGE

TECHNICAL FIELD

This invention relates to slide valves equipped in a syringe, more particularly to an intermediate slide valve and a plunger valve in direct contact with injection liquids and to syringes equipped with such slide valves, thereby said injection liquids nor valves being not affected with each other.

BACKGROUND OF THE INVENTION

There have been conventionally used plural segment type syringes in which a plurality of injection liquids, medicines, other dissolving liquids, etc. are kept in a plurally segmented syringe in advance, so that each liquid is mixed upon injection or a plurality of injection liquids can be dosed continuously by one shot operation.

According to an above mentioned conventional syringe, inside thereof is separated by intermediate slide valves into a plurality of segments in which each of injection liquids are charged separately.

There has been proposed an intermediate slide valve in Japanese Patent A No. 6-343,677, in which a synthetic resin film is conventionally laminated on a liquid contact surface of the intermediate slide valve, while a body end portion directly continued from the liquid contacting surface is not laminated with the synthetic resin film and is exposed as an elastic naked surface, that is to say, the elastic naked surface is exposed in a ring-like form on the body end portion.

DISCLOSURE OF THE INVENTION

Problems to be Solved by the Invention

According to the above mentioned intermediate slide valve, a ring belt portion of plunger head portion, which is in direct contact with an injection liquid, is formed as an elastic naked surface, thereby slidability and airtight properties of the valve being kept compatibly.

It is difficult, however, to completely prevent the elastic naked surface from contacting with the injection liquid because of exposure of said surface to the plunger head portion. For example, when the injection liquid is preserved in the syringe for a long time, not only soluble substances blended in the elastic body might be eluted in the liquid but also such elution would cause a drop in properties of the intermediate slide valve itself so that functions required to the intermediate slide valve can not be achieved completely.

In addition to the above mentioned plural segment type syringe, there has been jointly used a plunger equipped with a slide valve at the tip even in the case of a syringe of mono-segment type, in which a barrel is not segmented by the intermediate slide valve. In such a slide valve fitted on the plunger head (hereinafter referred to as a plunger slide valve), it is also difficult to fully prevent the elastic naked surface from contacting with the injection liquid because of exposure of said surface to the plunger head portion similarly as the above mentioned intermediate slide valve, when a synthetic resin film is laminated only on a surface in contact with the injection liquid. Here again, not only soluble substances blended in the elastic body might be eluted in the liquid but also such elution would cause a drop in properties of the intermediate slide valve itself.

Accordingly, it is an object of this invention to solve conventional problems as described above and to provide slide valves, i.e., an intermediate slide valve and a plunger slide valve, which can keep quality of injection liquid and, in addition, sustain functions required to these valves for a long period of time when the injection liquid is preserved in a syringe for a long time, and to provide a single or plural segment type syringe equipped with such slide valves.

Means to Solve Problems

This invention provides an intermediate slide valve equipped in a barrel of a plural segment type syringe to segment the syringe to plural segments and a plunger valve equipped in a barrel of plural or single segment type and a syringe equipped with said slide valve as will be described in the following.

1. A slide valve to be equipped in a syringe barrel which comprises an approximately cylindrical first elastic body and an approximately cylindrical second elastic body jointed to one bottom surface of said first elastic body, the other bottom surface of said first elastic body and a side surface portion continued from said bottom surface being laminated with a synthetic resin film and at least a side surface portion of said second elastic body being laminated with a synthetic resin film.
2. A slide valve described in the above item 1 in which said first elastic body and said second elastic body are jointed by fitting a ring-like concave portion and a ring-like convex portion formed on said bottom surfaces.
3. A slide valve described in the above item 1 in which a jointing portion between said first elastic body and said second elastic body is formed so as not to come into contact with an inner wall of a barrel when said slide valve is inserted into the said barrel.
4. A slide valve described in the above item 1 in which said slide valve is a plunger slide valve, a plunger joint hole being formed on one bottom surface (or on a bottom surface where said first elastic body and said second material are not jointed in the case of above item 2) and said bottom surface and a side surface portion continued from said bottom surface being laminated with a synthetic resin film.
5. A syringe equipped with a slide valve or valves described in above items 1 to 4.

A intermediate slide valve or a plunger slide valve used in this invention, both of which will be referred to as a slide valve simply in some cases, is an approximately cylindrical elastic body and a side surface portion thereof is covered with a synthetic resin film so that contact of an injection liquid with the elastic body of the slide valve is prevented when the slide valve is inserted into a barrel of a syringe of plural or single segment type, both of which will be referred to as a syringe simply in some cases. Said side surface portion means a portion continued from both bottom surfaces of the elastic body in the case of the intermediate slide valve and a portion continued from one bottom surface thereof in the case of the plunger slide valve. Because of the above mentioned construction, it is possible to prevent elution of soluble substances blended in the slide valve into the injection liquid and to preserve quality of the injection liquid over a long term storage thereof in the syringe, while properties of the slide valve can be kept.

The slide valve comprises the first elastic body and the approximately cylindrical second elastic body which is jointed with one bottom surface of the first elastic body, side surface portions continued from non-joint bottom surfaces of the first and the second elastic bodies are covered with the synthetic resin film.

In the case of the intermediate slide valve, not jointing bottom surfaces of the first and second elastic bodies are covered with the synthetic resin film and, in the case of the plunger slide valve, the other bottom surface, or not jointing one, of the first elastic body is covered with the film and that of the second elastic body, where is not jointed and formed a plunger joint hole, is may be covered with the synthetic resin film if necessary.

Contact of the injection liquid with the elastic body is successfully prevented by means of these intermediate and plunger slide valves of the invention when these valves are inserted into the barrel and, as a result, no soluble substance blended in the valves elutes in the injection liquid so that not only quality thereof but also properties of the valves can be kept even when the liquid is stored in the syringe for a long period of time.

Although jointing bottom surfaces of the first and the second elastic bodies are flat in shape and strongly jointed by, for example, simply press-contacting each other with heating, there may be formed a convex ring portion on the bottom surface of one elastic body such as the first one and a concave ring portion on the bottom surface of the other elastic body such as the second one, respectively, to joint them by fitting together. When a diameter of the convex portion is little bit larger than that of the concave portion, fitting between both portions is secured due to elasticity of the first and the second elastic bodies without causing disconnection thereof.

Such a fitting situation of the convex and the concave portions makes the first and the second elastic bodies to joint more strongly. The convex and the concave portions may be in the form of various rings such as a continuous or discontinuous circular, rectangular, triangular or polygonal ring, or various columns such as a pillar, rectangular pillar, triangular pillar or polygonal pillar, or may be formed into any other shape.

It is preferable to form the slide valve of this invention so as not to contact the jointing portion of the first and the second elastic bodies with an inner surface of the barrel when the valve is inserted therein.

The above mentioned construction makes it possible to decrease friction caused by the intermediate and the plunger slide valves when they are slid, thereby resulting in improved slidability without applying any lubricant such as silicone oil.

According to the present plural segment type syringe, the barrel is segmented to plural segments by means of the intermediate slide valves and the plunger slide valve as described above may be used therewith, while in the case of a single segment type, similar one may be used as the plunger slide valve.

As has been described above, it is possible to prevent the injection liquid stored in each segment of the plural segment type syringe from contacting with elastic bodies of the intermediate and the plunger slide valves. Similarly, the injection liquid stored in the barrel of the single segment type syringe can be prevented from contacting with the elastic body of the plunger slide valve. Accordingly, no soluble substance blended in these valves elutes in the injection liquid, thereby quality of the liquid and, in addition, properties of the valves being kept even when the liquid is stored in the syringe for a long period of time.

Effects of the Invention

According to this invention, the intermediate slide valve comprising both bottom surfaces of the approximately cylindrical elastic body and the side surface portion continued from each of the bottom surfaces are covered with the synthetic resin film, while the plunger slide valve comprising at least one bottom surface of the approximately cylindrical elastic body and the side surface portion continued from the bottom surface are covered with the synthetic resin film, thereby quality of the injection liquid and properties of such valves themselves being kept without causing elution of soluble substances blended in the valves to the injection liquid even when the liquid is kept in the syringe for a long period of time.

BRIEF DESCRIPTION OF THE DRAWINGS

FIG. 4 is a sectional view of a plunger slide valve according to an embodiment of the invention.

Figure 1:
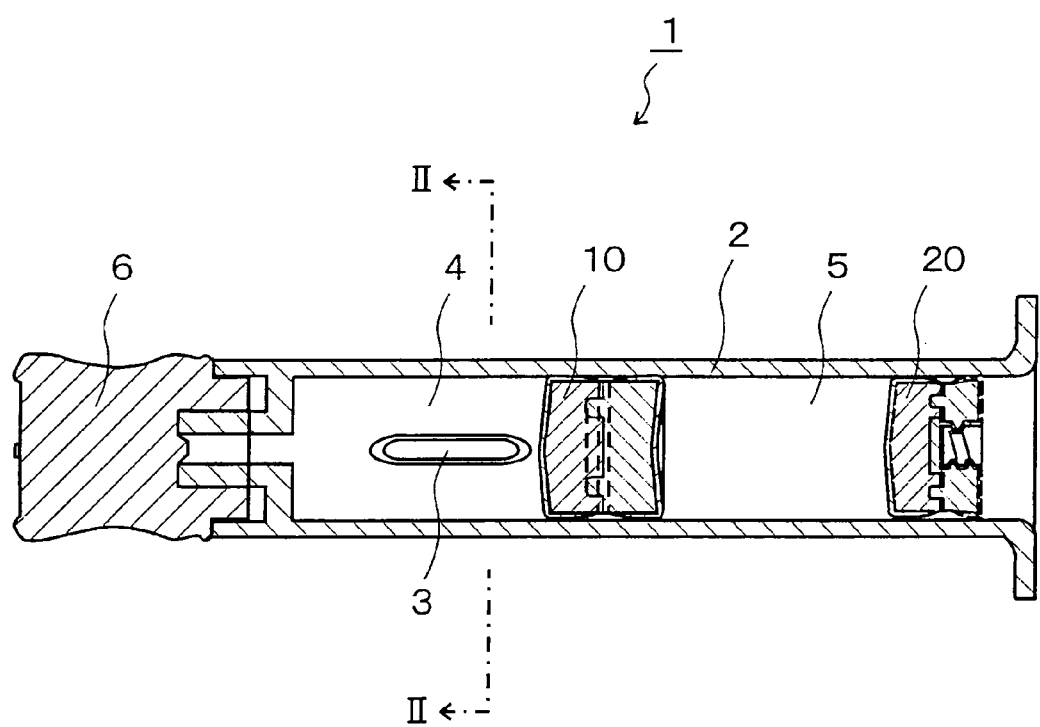
FIG. 1 is a schematic sectional view of a plural segment type syringe according to an embodiment of the invention in which an intermediate slide valve is used.

DESCRIPTION OF NUMBERED ELEMENTS 1. two-segment type syringe
2. barrel
3. by-pass passage
4. first segment (forward chamber)
5. second segment (backward chamber)
6. nozzle cap
10. intermediate slide valve
11. first member
12. second member
13. first elastic body
14. second elastic body
15, 16, 25, 26 synthetic resin film
17. concave portion
18. convex portion
20. plunger slide valve
21. third member
22. fourth member
23. third elastic body
24. fourth elastic body
27. concave portion
28. convex portion
29. plunger jointing hole

MOST PREFERRED EMBODIMENTS OF THE INVENTION

Referring now to the drawings, this invention will be detailed using the following preferred embodiments. The same elements will be designated by the same symbols in the drawings and duplication of their description will be omitted. There will be described a two-segment type syringe as an embodiment in which an intermediate slide valve is used to mix two kinds of injection liquids upon injection. A needle locking side of the syringe and a plunger inserting side will be described as forward and backward, respectively, in some cases in this invention.

First of all, referring to FIG. 1, there will be described a construction of the two-segment type syringe 1 in which an intermediate slide valve 10 and a plunger slide valve 20 of the embodiment are used. FIG. 1 is a schematic sectional view of the two-segment type syringe 1.

The two-segment type syringe 1 comprises a barrel 2, the intermediate slide valve 10 inserted slidably in the barrel 2 at an approximately central position thereof and the plunger slide valve 20 inserted slidably therein toward an opening side at a backward position from the intermediate slide valve 10. That is to say, the inside of the barrel 2 is segmented to two segments by means of the plunger slide valve 20.

A rubber stopper 6 is fitted to a tip portion of the barrel 2. The first injection liquid (forward injection liquid) is charged and stored in the first segment 4 segmented by means of an inner surface of the barrel 2, the rubber stopper 6 fitted to seal the tip portion of the barrel 2 and the intermediate slide valve 10. On the other hand, the second injection liquid (backward injection liquid) is charged and stored in the second segment 5 segmented by means of the inner surface of the barrel 2 and the plunger slide valve 20.

There is provided a by-pass passage 3 formed by a concave by-pass in the first segment 4 of the barrel 2. About one to four by-pass passages are formed in the inner wall of the first segment parallel to the axial direction of the barrel 2.

The intermediate slide valve 10 moves forward of the syringe 2 by an injecting operation and is inserted to a by-pass passage forming section, thereby the by-pass passage 3 being formed to by-pass the intermediate slide valve 10. The second injection liquid charged and stored in the second segment 5 of the barrel 2 is injected into the first segment 4 through the by-pass passage 3 to dissolve mixed with the forward injection liquid, which is then applied to a human body.

The intermediate slide valve 10 will be described by referring to FIGS. 2 and 3. FIG. 2 is a sectional view of the intermediate slide valve 10 and FIG. 3 is an illustration of a jointing manner of the first elastic body 13 and the second one 14 comprising the valve 10.

The intermediate slide valve 10 comprises the first and the second elastic bodies 13 and 14 in approximately cylindrical shape which are jointed together through bottom surfaces 13c and 14c, respectively, while the other bottom surface, i.e., not jointing bottom surface 13a of the first elastic body 13 and a side surface portion 13b continued from the bottom surface 13a are laminated with a synthetic resin film 15, and the other bottom surface, i.e., not jointing bottom surface 14a of the second elastic body 14 and a side surface portion 14b continued from the bottom surface 14a is also laminated with a synthetic resin film 16. The first and the second elastic bodies 13 and 14 laminated with synthetic resin films 15 and 16 will be in some cases referred to as the first member 11 and the second member 12, respectively.

As is described above, the intermediate slide valve 10 is formed by jointing the bottom surface 13c of the first elastic body 13 comprising the first member 11 and the bottom surface 14c of the second elastic body 14 comprising the second member 12.

Figure 2A:
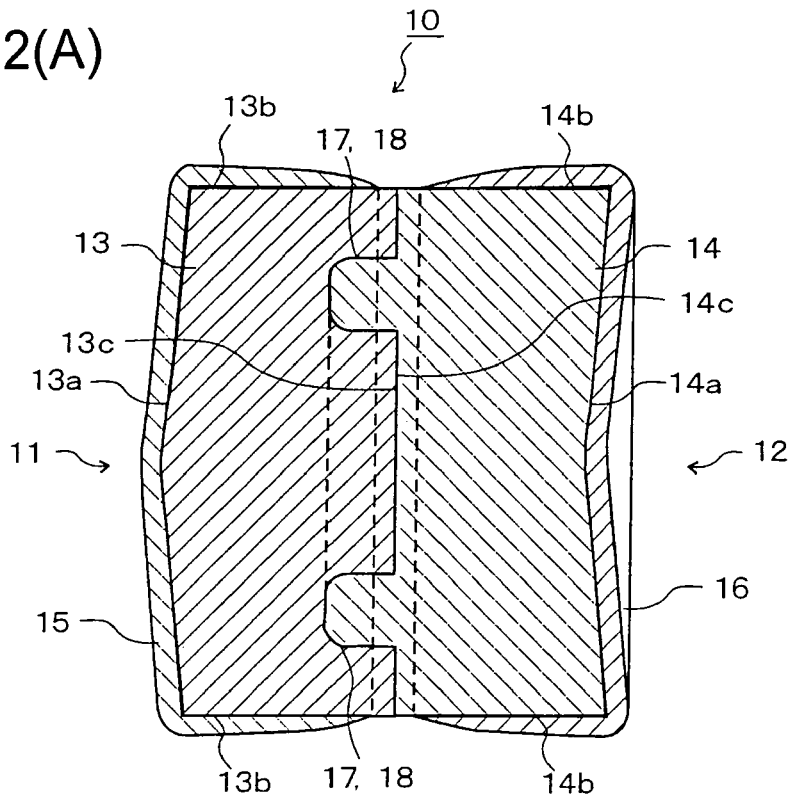
FIG. 2 is a sectional view of an intermediate slide valve according to an embodiment of the invention, in which convex and concave portions are formed in A and are not formed in B.
Figure 3A:
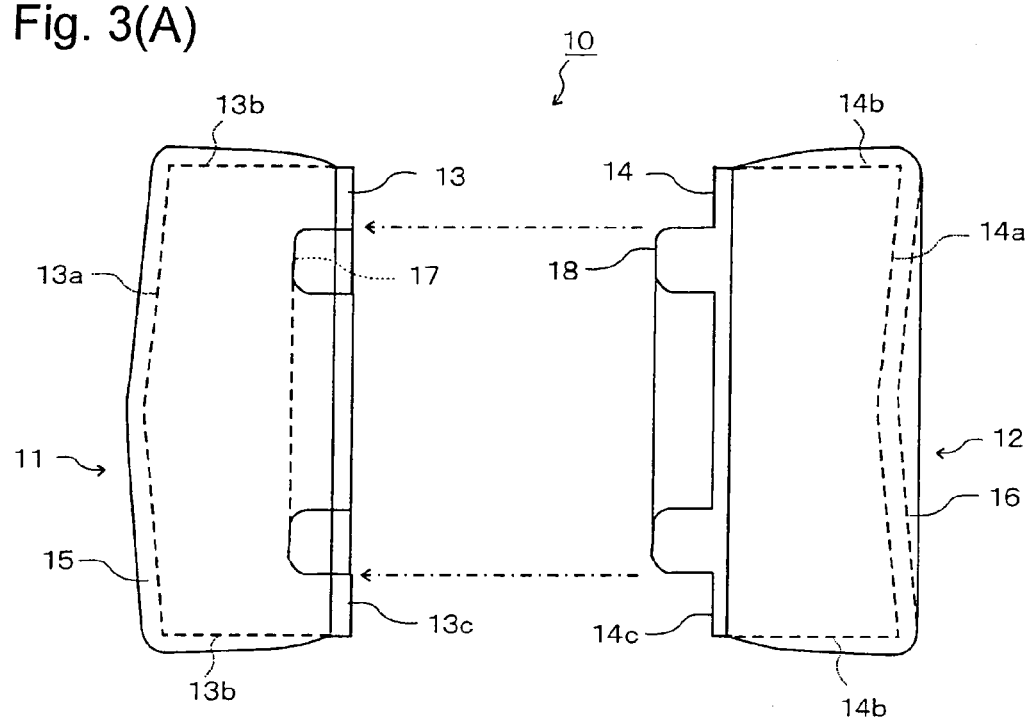
FIG. 3 is an illustration of a jointing manner of the first and the second materials according to an embodiment of the invention, in which convex and concave portions are formed in A and are not formed in B.

A ring-like concave portion 17 is formed on the bottom surface (jointing bottom surface) 13c of the first elastic body 13, while a ring-like convex portion 18 is formed on the bottom surface (jointing bottom surface) 14c of the second elastic body 14 as shown in FIGS. 2(A) and 3(A). These ring-like concave and convex portions 17 and 18 are fitted each other when the first and the second elastic bodies 13 and 14, i.e., the first and the second members 11 and 12, are jointed.

Figure 2B:
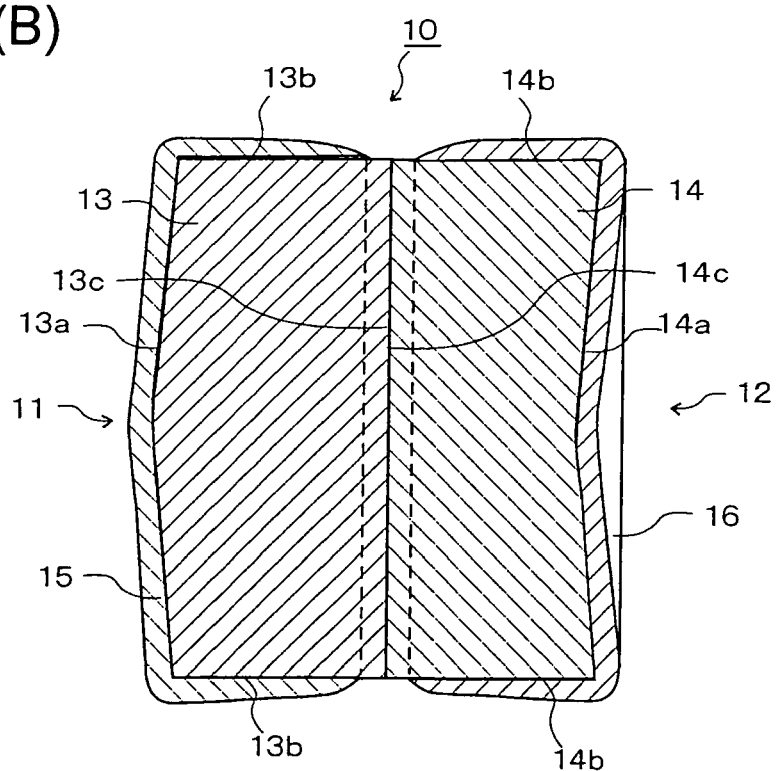
Figure 3B:
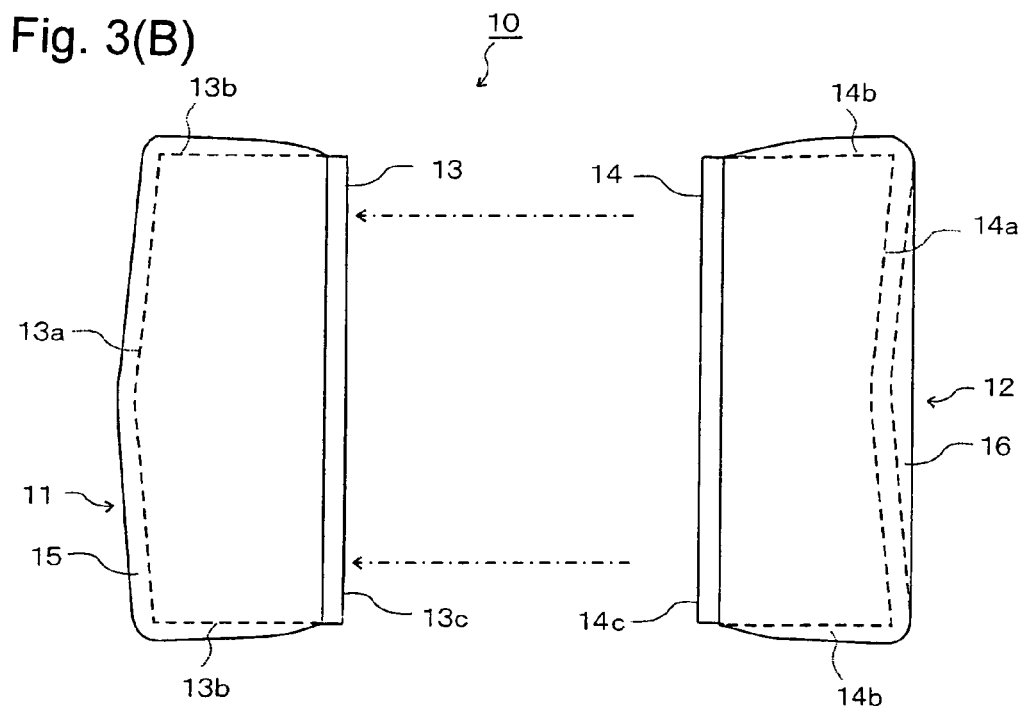

The first elastic body 13 and the second one 14 may be jointed, for example, by means of adhesive- or heat-fusing without using such concave and convex portions 17 and 18 (see, FIGS. 2(B) and 3(B)), or also be prepared by monolithic molding (not shown). Further, the jointing bottom surfaces 13c and 14c including both concave and convex portions 17 and 18 may be laminated with the synthetic resin film.

In FIGS. 2(B) and 3(B), the jointing bottom surfaces 13c and 14c of the first and the second elastic bodies 13 and 14 are flat, in which they are faced in contact with each other and jointed by means of adhesive- or heat-fusing without forming the concave and convex portions 17 and 18.

Referring to FIG. 4, the present plunger slide valve 20 will be detailed. The plunger slide valve 20 comprises the first and the second elastic bodies 23 and 24 in approximately cylindrical shape which are jointed through bottom surfaces thereof 23c and 24c. The other bottom surface 23a, i.e., not jointing bottom surface, of the first elastic body 23 and a side surface portion 23b continued from the bottom surface 23a are laminated with a synthetic resin film 25. The thus laminated first elastic body 23 will be in some cases referred to as the first member 21.

There is formed a plunger jointing hole 29 on the other bottom surface 24a, i.e., not jointing bottom surface, of the second elastic body 24. The bottom surface 24a and a side surface 24b continued therefrom are laminated with a synthetic resin film 26, which will be in some cases referred to as the second member 22.

Although it is not always necessary to laminate the synthetic resin film on the bottom surface 24a of the second elastic body 24 where the plunger jointing hole 29 is formed, the bottom surface 24a including the plunger jointing hole 29 is preferably laminated.

The plunger slide valve 20 is also formed by jointing one bottom surface 23c of the first elastic body 23 comprising the first member 21 and one bottom surface 24c of the second elastic body 24 comprising the second member 22.

A ring-like concave portion 27 is formed on the bottom surface (jointing bottom surface) 23c of the first elastic body 23, while a ring-like convex portion 28 is formed on the bottom surface (jointing bottom surface) 24c of the second elastic body 24. These ring-like concave and convex portions 27 and 28 are fitted each other when the first and the second elastic bodies 23 and 24, i.e., the first and the second members 21 and 22, are jointed.

Similarly as the intermediate slide valve 10 as shown in FIGS. 2(B) and 3(B), the first elastic body 23 and the second one 24 may be flat and faced in contact with each other to joint, for example, by means of adhesive- or heat-fusing without forming such concave and convex portions 27 and 28 (not shown), or also be prepared by monolithic molding. Further, the jointing bottom surfaces 23c and 24c including both concave and convex portions 27 and 28 may be laminated with the synthetic resin film.

There will be then described materials of the first and the second elastic bodies 13, 14, 23 and 24 used to comprise the intermediate slide valve 10 and the plunger slide valve 20.

There may be used the following materials alone or as a mixture or alloy thereof to prepare the first and the second elastic bodies 13, 14, 23 and 24: natural rubber (NR), polyisoprene (IR), polybutadiene (BR), styrene-butadiene copolymer rubber (SBR), styrene-isoprene copolymer rubber (SIR), ethylene-propylene non-conjugated copolymer rubber (EPDM), isobutylene-isoprene copolymer rubber (IIR), chlorinated IIR rubber (CIIR), brominated IIR rubber (BIIR), butadiene-acrylonitrile copolymer rubber, (NBR), hydrogenated NBR, SBS, SEBS, SIBS and the like.

It is preferable to blend various kinds of blending agents to starting elastomers of the above mentioned materials to form their compositions, which are then crosslinked by means of sulfur, sulfur-containing crosslinking agents, organic peroxides, electron rays, etc. to yield high resilient products. With regard to resilient index thereof, the compression set is less than 40% determined according to Japanese Industrial Standard (JIS) K 6262 (2006). Preferred hardness of these materials is 25 to 65 determined according to JIS K 6253 (1997).

A crosslinking manner to yield the elastic bodies 13, 14, 23 and 24 includes heating and pressing in a die and dynamic crosslinking in an injection molder or kneader.

The synthetic resin films 15, 16, 25 and 26 to be laminated on the elastic bodies 13, 14, 23 and 24 preferably include high hygienic and high slidable materials such as, for example, fluororesin, polyethylene resin, polypropylene resin (PP) including homopolymer and copolymer with an ethylene, butylene or other group, polyester resin (PET), polysulfone resin (PSF), polymethylpentene resin (PMP), polyacrylate resin (PAR), polyamide resin (PA), modified polyphenyleneoxide resin ((PPE), resins comprising a cyclic olefin compound or crosslinked polycyclic hydrocarbon compound as a polymerizing component, polycarbonate resin (PC) and polar group-grafted polyolefin resin. Especially preferable resin is fluroresin and ultra high molecular polyethylene resin of 1,000,000 to 7,000,000 in molecular weight.

Thickness of the synthetic resin films 15, 16, 25 and 26 is preferably about 0.01 to 0.3 mm.

There may be used conventional materials well known in the art for remaining parts other than the intermediate slide valve 10 and the plunger slide valve 20. A material useful for the barrel 2 may includes glass, plastics such as cyclic olefin resin (COC, COP), polymethylpentene resin, polypropylene resin, propylene-ethylene copolymer resin, polyester resin, polyether-sulfone resin, polysulfone resin, or laminate of two or more layers comprising above mentioned resins and a resin selected from polyamide resin, polyvinyl alcohol resin and saponified ethylene-vinyl acetate.

The intermediate slide valve 10 and the plunger valve 20 may be prepared as in the following.

In the case of the intermediate slide valve 10, a synthetic resin film and an elastic body molding sheet are superimposed and subjected to press molding, followed by cutting periphery thereof under a tensioned condition to form the first member 11. After the second member 12 is formed in a similar manner as described above, the bottom surface 13c of the first elastic body 13 comprising the first member 11 is jointed to the bottom surface 14c of the second elastic body 14 comprising the second member 12.

As the synthetic resin film and the elastic body molding sheet are cut under a tensioned condition, an outer diameter of one bottom surface 13c, i.e., jointing bottom surface, is formed smaller than that of the other bottom surface 13a, i.e., not jointed surface of the first elastic body 13 comprising the first member 11 because of restoring force of the film and the sheet. Similarly, an outer diameter of one bottom surface 14c, i.e., jointing bottom surface, is formed smaller than that of the other bottom surface 14a, i.e., not jointed surface of the second elastic body 14 comprising the second member 12 because of restoring force of the film and the sheet. The bottom surfaces 13c and 14c of smaller diameter are jointed each other as each jointing bottom surface so that a jointing portion of the first and the second elastic bodies 13 and 14 does not come into contact with an inner surface of the barrel 2 when the intermediate slide valve 10 is inserted therein.

In the case of the plunger slide valve 20, the first member 11 and the second member 12 are molded and then the bottom surface 23c of the third elastic body 23 comprising the first member 11 and the bottom surface 24c of the fourth elastic body 24 comprising the second member 12 are jointed in a similar manner as described above Here again, as the synthetic resin film and the elastic body molding sheet are cut under a tensioned condition, an outer diameter of one bottom surface 23c, i.e., jointing bottom surface, is formed smaller than that of the other bottom surface 23a, i.e., not jointed surface of the first elastic body 23 comprising the first member 11 because of restoring force of the film and the sheet. Similarly, an outer diameter of one bottom surface 24c, i.e., jointing bottom surface, is formed smaller than that of the other bottom surface 24a, i.e., not jointed surface of the second elastic body 24 comprising the second member 22 because of restoring force of the film and the sheet. The bottom surfaces 23c and 24c of smaller diameter are jointed each other as each jointing bottom surface so that a jointing portion of the first and the second elastic bodies 23 and 24 does not come into contact with an inner surface of the barrel 2 when the plunger slide valve 20 is inserted therein.

When two kinds of injection liquids or other medical contents charged and kept in the above mentioned two-segment type syringe 1 are applied, a plunger (not shown) is fitted in the plunger jointing hole 29 of the plunger slide valve 20, which is then pressingly inserted into the barrel 2 by means of the plunger while keeping a nozzle cap 6 in a capped situation. Thus, the intermediate slide valve 10 moves forward and approaches to a by-pass passage forming portion, thereby a by-pass passage 3 being opened to flow the injection liquid in a backward segment 5 into a forward segment 4 and mix the two contents kept in the forward and the backward segments 4 and 5. If the content of the forward segment 4 is solid, the syringe 2 is fully shaken in this situation to dissolve the solid completely. The nozzle cap 6 is then taken off to fit an injection needle and inject the mixture to a human body.

According to the intermediate slide valve 10 and the plunger slide valve 20 of the present embodiment, each bottom surface 13a and 14a of the first and the second elastic bodies 13 and 14 of the intermediate slide valve 10 as well as each side surface portion 13b and 14b continued from the bottom surfaces 13a and 14a are laminated with the synthetic resin films 15 and 16, while each bottom surface 23a and 24a of the first and the second elastic bodies 23 and 24 of the plunger slide valve 20 and each side surface portion 23b and 24b continued from the bottom surfaces 23a and 24a are laminated with the synthetic resin films 25 and 26 are laminated with the synthetic resin films 25 and 26, so that the first and the second elastic bodies 13 and 14 of the intermediate slide valve 10 as well as the first and the second elastic bodies 23 and 24 of the plunger slide valve 20 never come in contact with the injection liquids or other medical contents kept in the forward and the backward segments 4 and 5 when the barrel 2 is sealed by means of the plunger slide valve 10 after charging the medical content in the first segment (forward chamber) 4 and inserting the plunger slide valve 10 into the barrel 2 of the two-segment type syringe 1, followed by charging the injection liquid in the second segment (backward chamber) 5. As a result, no soluble substance blended in the elastic bodies 13, 14, 23 and 24 elutes in the injection liquid so that not only quality of the injection liquid but also properties of these valves 10 and 20 can be kept even when the injection liquid is stored in the syringe 1 for a long period of time.

Further, in the case of the intermediate slide valve 10 provided with the ring-like concave and the convex portions 17 and 18, the first and the second elastic bodies 13 and 14 can be jointed more strongly by fitting these ring-like portions 17 and 18 and, in the case of the plunger slide valve 20 provided with the ring-like concave and the convex portions 27 and 28, the first and the second elastic bodies 23 and 24 can be jointed more strongly by fitting these ring-like portions 27 and 28.

When diameters of the convex portions 18 and 28 are formed slightly largely compared with those of the concave portions 17 and 27, a fitting situation of the first elastic bodies 13 and 23 and the second elastic bodies 14 and 24 is further improved because of elasticity thereof without causing disconnection between the concave portions 17 and 27 and the convex portions 18 and 28.

Owing to the intermediate slide valve 10 of this invention, the jointing portions of the first and the second elastic bodies 13 and 14 do not come into contact with the inner surface of the barrel 2, while owing to the plunger slide valve 20 of this invention, the jointing portions of the first and the second elastic bodies 23 and 24 do not come into contact with the inner surface of the barrel 2, thereby reducing friction caused by sliding the intermediate slide valve 10 and the plunger slide valve 20 and securing improved slidability.

According to the two-segment type syringe 1 of this invention, the present intermediate slide valve 10 is used to segment the barrel 2 to two segments so that contact of the injection liquids stored in the thus segmented each segment 4 and 5 with the first and the second elastic bodies 13 and 14 of the valve 10 can be prevented and, in addition, the present plunger slide valve 20 is used so that contact of the injection liquid stored in the second segment (backward chamber) 5 with the first and the second elastic bodies 23 and 24 of the valve 20 can be prevented. As a result, no soluble substance blended in these elastic bodies elutes and not only quality of the injection liquids but also properties of these valves 10 and 20 can be kept even when the injection liquid is stored in the syringe 1 for a long period of time.

This invention has been detailed through the embodiment as described above but is not restricted by the embodiment and may be variously modified. For example, the intermediate slide valve 10 may be applied to a sequentially dispensing syringe in which two or more kinds of injection liquids are injected in order by a single shot operation, although the valve 10 is used for the two-segment type syringe in which the injection liquids are mixed. Numbers of segments segmented by the intermediate slide valve 10 is not limited to two but may be three or more.

Further, the intermediate slide valve 10 comprises the first member 11 and the second member 12 according to the embodiment, but may comprise a single member without dividing it into two. It is also possible to properly modify and embody this invention without departing from the scope of the invention.

The syringe of this invention may be a mono-segment type (not shown) in which only the present plunger slide valve 20 is used but the intermediate slide valve 10 is not used.

What is claimed is:

1. A slide valve disposed in a syringe barrel, the slide valve comprising:
   an approximately cylindrical first elastic body having a first bottom surface and a second bottom surface opposite to the first bottom surface, and an approximately cylindrical second elastic body jointed to the first bottom surface of said first elastic body, the second bottom surface of said first elastic body and a side surface portion contiguous with said second bottom surface being laminated with a first, synthetic resin film and at least a side surface portion of said second elastic body being laminated with a separate second synthetic resin film,
   wherein a portion of the side surface portion of the first elastic body and a portion of the side surface portion of the second elastic body respectively proximate a jointing portion between the first and second elastic bodies, are lamination free and have diameters which are respectively less than diameters of the laminated portions of the side surface portions of the first elastic body and the second elastic body.

2. A slide valve as claimed in claim 1, in which said first elastic body and said second elastic body are jointed by fitting a ring-like concave portion and a ring-like convex portion formed on said bottom surfaces.

3. A slide valve as claimed in claim 1, in which the jointing portion between said first elastic body and said second elastic body is formed so as not to come into contact with an inner wall of a barrel when said slide valve is inserted into said barrel.

4. A slide valve as claimed in claim 1, in which said slide valve is an intermediate slide valve for segmenting a barrel of a plural segment type syringe to a plurality of segments.

5. A slide valve as claimed in claim 1, in which said slide valve is a plunger slide valve having a plunger joint hole formed on one bottom surface thereof and said one bottom surface and a side surface portion contiguous with said one bottom surface is laminated with the second synthetic resin film.

6. A syringe equipped with a slide valve as claimed in claim 1.

7. A slide valve as claimed in claim 1, wherein the first synthetic resin film and the second synthetic resin film are respectively press molded films.

8. A slide valve as claimed in claim 1, wherein the first synthetic resin film and the second synthetic resin film consist of at least one of fluororesin, polyethylene resin, polypropylene resin including homopolymer and copolymer with an ethylene, butylene or other group, polyester resin, polysulfone resin, polymethylpentene resin, polyacrylate resin, polyamide resin, modified polyphenyleneoxide resin, resins comprising a cyclic olefin compound or crosslinked polycyclic hydrocarbon compound as a polymerizing component, polycarbonate resin or polar group-grafted polyolefin resin.

9. A slide valve as claimed in claim 8, wherein the first synthetic resin film and the second synthetic resin film consist of at least one of fluroresin or ultra high molecular polyethylene resin of 1,000,000 to 7,000,000 in molecular weight.

10. A slide valve as claimed in claim 1, wherein the first synthetic resin film and the second synthetic resin film respectively have a thickness of about 0.01 to 0.3 mm.

* * * * *